United States Patent
Shih et al.

(10) Patent No.: US 8,772,514 B2
(45) Date of Patent: Jul. 8, 2014

(54) PREPARATION OF FURFURAL COMPOUNDS, AND MIXTURE FOR PREPARING THE SAME

(75) Inventors: Ruey-Fu Shih, New Taipei (TW); Hsi-Yen Hsu, Hsinchu (TW); Jinn-Jong Wong, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 60 days.

(21) Appl. No.: 13/275,085

(22) Filed: Oct. 17, 2011

(65) Prior Publication Data

US 2013/0023679 A1     Jan. 24, 2013

(30) Foreign Application Priority Data

Jul. 21, 2011 (TW) .............................. 100125871 A

(51) Int. Cl.
C07D 307/48 (2006.01)
(52) U.S. Cl.
USPC .......................................................... 549/489
(58) Field of Classification Search
USPC .................................................. 549/488, 489
See application file for complete search history.

(56) References Cited

U.S. PATENT DOCUMENTS

| | | | |
|---|---|---|---|
| 2008/0033187 A1 | 2/2008 | Zhao et al. | |
| 2009/0313889 A1 | 12/2009 | Zhang et al. | |
| 2010/0004437 A1 | 1/2010 | Binder et al. | |
| 2012/0004430 A1 | 1/2012 | Zhang et al. | |

FOREIGN PATENT DOCUMENTS

| | | | |
|---|---|---|---|
| CN | 101386611 | | 3/2009 |
| CN | 10181106 A | * | 8/2010 |
| CN | 101811066 A | * | 8/2010 |
| JP | 6-511043 | | 12/1994 |
| JP | 2011-524900 | | 9/2011 |
| WO | WO 2008/019219 | | 2/2008 |

OTHER PUBLICATIONS

Kuster, Carbohydrate Research, vol. 54(2), p. 177-183 (1977).*
Hu et al, Green Chemistry, vol. 11, p. 873-877 (2009).*
Kuster et al, Die Starke, vol. 29(5), p. 172-176 (1977).*
Mednick et al, J. of Org. Chem., vol. 27., p. 398-402 (1962).*
English language translation of abstract of CN 101386611 (published Mar. 18, 2009).
Zhao, H., et al.; "Metal Chlorides in Ionic Liquid Solvents Convert Sugars to 5-Hydroxymethylfurfural;" Sciencemag.org; vol. 316; Jun. 15, 2007; pp. 1596-1600.
Hu, S., et al.; "Conversion of Fructose to 5-Hydroxymethylfurfural Using Ionic Liquids Prepared from Renewable Materials;" Green Chemistry; 2008; pp. 1280-1283.
Qi, X., et al.; "Efficient Process for Conversion of Fructose to 5-Hydroxymethylfurfural with Ionic Liquids;" Green Chemistry; 2009; pp. 1327-1331.
Binder, J.B., et al.; "Simple Chemical Transformation of Lignocellulosic Biomass into Furans for Fuels and Chemicals;" Journal of the American Chemical Society; 2009; pp. 1979-1985.
Ohno, H.; "Importance and Possibility of Ionic Liquids;" Electrochemical Aspects of Ionic Liquids; pp. 1-2, (2005).
Angell, C.A., et al.; "Physical Chemistry of Ionic Liquids, Inorganic and Organic, Protic and Aprotic;" Electrochemical Aspect of Ionic Liquids; 2005; pp. 5.
Wasserscheid, P., et al.; "Ionic Liquids in Synthesis;" 2007; pp. 836-920.
Brennecke, J.F., et al.; "Ionic Liquids: Innovative Fluids for Chemical Processing;" Nov. 2001; vol. 47; No. 11; pp. 2384-2389.
Chidambaram, M., et al.; "A Two-Step Approach for the Catalytic Conversion of Glucose to 2, 5-Dimethylfuran in Ionic Liquids;" Green Chemistry; 2010; pp. 1253-1262.
Qi, et al.: "Efficient Catalytic Conversion of Fructose into 5-Hydroxymethylfurfural in Ionic Liquids at Room Temperature"; copyright 2009 Wiley-VCH Verlag GmbH& Co. KGaA, Weinheim ChemSusChem 2009, 2, pp. 944-946.
JP Office Action dated Aug. 13, 2013.
English Abstract translation of JP6-511043 (Published Dec. 8, 1994).
English Abstract translation of JP2011-524900 (Published Sep. 8, 2011).
Clement Lansalot-Matras, et al.: "Dehydration of fructose into 5-hydroxymethylfurfural in the presence of ionic liquids"; Catalysis Communications 4 (2003) 517-520.
Yingzhao, et al.: "Preparation of 5-hydroxymethylfurfural from glucose in ionic liquid"; China Academic Journal Electronic Publishing House; Copyright 1994-2011; Chemical Industry and Engineering Progress; pp. 552-556.
TW Office Action dated Apr. 17, 2013.
Rosatella, et al.: "5-Hydroxymethylfurfural (HMF) as a building block platform: Biological properties, synthesis and synthetic applications"; Green Chemistry; 2011.

* cited by examiner

*Primary Examiner* — Golam M M Shameem
(74) *Attorney, Agent, or Firm* — McClure, Qualey & Rodack, LLP

(57) ABSTRACT

A method of preparing furfural compounds and a mixture for preparing the same are disclosed. First, a solution is prepared by mixing an organic ammonium salt and a hydroxyl organic solvent. Then, a carbohydrate is mixed with the solution to form a mixture. The mixture is heated to a reaction temperature for conversion of the carbohydrate to produce the furfural compounds.

9 Claims, No Drawings

PREPARATION OF FURFURAL COMPOUNDS, AND MIXTURE FOR PREPARING THE SAME

This application claims the benefit of Taiwan application Serial No. 100125871, filed Jul. 21, 2011, the subject matter of which is incorporated herein by reference.

BACKGROUND

1. Technical Field

The disclosure relates in general to preparation of furfural compounds and mixture for preparing the same, and more particularly to a preparation method to improve the yield and lower the cost for production of furfural compounds.

2. Description of the Related Art

HMF (hydroxymethylfurfural) is one of furfurals. Furfural is an industrial chemical, which can be derived from a variety of agricultural byproducts. Furfural is also an aromatic aldehyde with chemical formula of $C_5H_4O_2$, and its cyclic structure is shown below. HMF can be prepared via the dehydration of fructose or glucose. Since the petroleum is gradually depleted nowadays, HMF has been noticed in the field of application of renewable energy. HMF is an organic compound with chemical formula of $C_6H_6O_3$. The structure of HMF, as shown below, includes a hydroxyl functional group, an aldehyde functional group and a heterocyclic ring composed of four C atoms and an O atom.

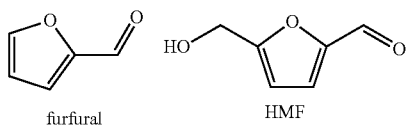

furfural    HMF

HMF, as one of furfural, will inhibit the growth of microorganisms in solution, thus cannot be synthesized by bio-fermentation. HMF can only be chemically conversed from carbohydrate with C6 sugars. However, the side reaction is hard to be controlled, thus the reaction efficiency is low and the isolation and purification is hard. Many famous chemical companies and research instruments have tried to breakthrough the technical obstacle of low HMF yield. Zhao et al. (US patent Pub. No. 2008/0033187) have disclosed the preparation of HMF in ionic liquids. The ionic liquid is solely composed of ions and the melting temperature of the ionic liquid must lower than 100° C., as defined in [1] Hiroyuki Ohno, Electrochemical aspects of Ionic liquids, Jone Wiley Sons, Inc., 2005., [2] Peter Wasserscheid and Tom Welton, Ionic liquids in synthesis, Wily-VCH, 2003., [3] Joan F. Brennecke, Edward J. Maginn, AIChE Journal, Vol. 47, 2001, p. 2384-2389., and [4] Stark, A.; Seddon, K. Ionic Liquids. In Kirk-Othmer Encyclopedia of Chemical Technology; JohnWiley and Sons: New York, 2007; Vol 26; pp 836-920. An ionic liquid, formed at the reaction temperature of about 100° C. by using the organic salt with melting temperature lower than 100° C., is used as solvent. The carbohydrate is converted to HMF by using the ionic liquid (as the solvent) and the chlorinated metal as catalyst. Zhang et al. (US patent Pub. No. 2009/0313889) have disclosed preparation of HMF by using ionic liquid as solvent and chromium complex of

SUMMARY

The disclosure is directed to a method of preparing furfural compounds and a mixture for preparing the same.

According to one embodiment, a method of preparing furfural compounds is provided. A solution is prepared by mixing an organic ammonium salt and a hydroxyl organic solvent. A carbohydrate is added to the solution to form a mixture. Then, the mixture is heated to a reaction temperature for conversion of the carbohydrate to the furfural compounds.

According to another embodiment, a mixture for preparing the furfural compounds is provided. The mixture at least comprises an organic ammonium salt, a hydroxyl organic solvent and a carbohydrate.

DETAILED DESCRIPTION

A method of preparing furfural compounds and a mixture for preparing the same are disclosed in the embodiment.

In an embodiment, a method of preparing furfural compounds (for example, HMF or furfural) comprises the following steps. An organic ammonium salt and a hydroxyl organic solvent are mixed to form a solution. Then, a carbohydrate is added to the solution to form a mixture. The mixture is heated to a reaction temperature for conversion of the carbohydrate to the furfural compounds, for example, HMF or furfural. The molar ratio of the organic ammonium salt to the hydroxyl organic solvent (organic ammonium salt/hydroxyl organic solvent) is in a range of 1 to 9 or a range of 2.5 to 4. The amount of the carbohydrate is 5-20 wt %, or 10 wt % of the mixture.

In an embodiment, the organic ammonium salt may be chain organic ammonium salt or cyclic organic ammonium salt.

In an embodiment, the chain organic ammonium salt is represented by the general chemical formula [III], and the cyclic organic ammonium salt is at least one of the compounds represented by the general chemical formula [I], [II] and [IV]:

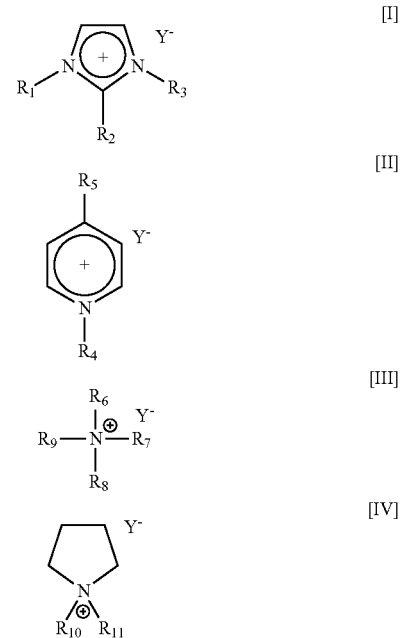

wherein $R_1$~$R_{11}$ are independently selected from, for example, hydrogen (H), alkyl functional group (for example, $C_1$-$C_6$ alkyl), cycloalkyl functional group, aryl functional group or alkaryl functional group. Also, those functional groups may optionally and selectively connect hydrogen, hydroxyl group (OH), chlorine (Cl), bromine (Br), iodine (I)

or cyano group (CN). The anion Y⁻ of the organic ammonium salt is, for example, fluoride (F⁻), chloride (Cl⁻), bromide (Br⁻), iodide (I⁻), nitrate ion ($NO_3^-$), hydrogen sulfate ($HSO_4^-$), tetrafluoroborate ($BF_4^-$), cyanide ion (CN⁻), trifluoromethanesulfonate ($SO_3CF_3^-$), or carboxylate trifluoromethanesulfonate ($COOCF_3^-$).

In an embodiment, the melting temperature of the organic ammonium salt is, for example, >100° C.

In an embodiment, the chain organic ammonium salt is, for example, comprise cycloalkyltrialkylammonium salt, aryltrialkylammonium salt, alkaryltrialkylammonium salt, tetraalkylammonium salt, or the combinations thereof.

In another embodiment, the chain organic ammonium salt is, for example, choline chloride, tetramethylammonium chloride, triethylmethylammonium chloride, benzyltriethylammonium chloride, or the combinations thereof.

In an embodiment, the cyclic organic ammonium salt is, for example, a heterocyclic ring-contained organic ammonium salt, and the heterocyclic ring-contained organic ammonium salt comprises a pyridinium functional group, an imidazolium functional group, or a pyrrolidinium functional group.

In another embodiment, the cyclic organic ammonium salt is, for example, 1-ethylpyridinium chloride, 1-butylpyridinium chloride, or the combinations thereof.

Besides, in the embodiment, the hydroxyl organic solvent comprises, for example, $C_2$-$C_6$ compounds of monohydric alcohols, diols, triols or polyalcohols (for example, ethylene glycol, propylene glycol or glycerol); or comprise compounds that contain ether group (—C—O—C—) on their carbon chains (for example, diethylene glycol or polyethylene glycol compound $HO(CH_2CH_2O)_nH$, n=1-15 (for example, PEG200, polyethylene glycol)).

After reaction in the embodiment, benzene or ether solvent can be used to extract HMF for the separation of HMF from the mixture. The isolation and purification is thus simplified.

Examples of the carbohydrates used in the embodiment include hexose, disaccharose, oligosaccharide, glycan, fructose, glucose, sucrose, starch, pentose and xylose. In an embodiment, an adapted catalyst can be added into the mixture depending on the kind of carbohydrate. The adapted catalyst may be acid catalyst, chloride or bromide containing chromium (Cr) compounds, chloride or bromide containing tin (Sn) compounds, or chromium complex of N-heterocyclic carbine as listed in Table 1. The acid catalyst used in the embodiment can be zeolite or sulfonic acid ion-exchange resin catalyst. In the embodiment, a mixture is formed by mixing the carbohydrate and the solution. Then, the mixture is heated at a reaction temperature lower than 180° C. for the conversion of the carbohydrate to HMF or furfural. In an embodiment, the reaction temperature is in a range of, for example, room temperature (for example, 25° C.) to 180° C., 80~140° C., 100~140° C., 120~140° C., or 80~120° C.

In some embodiments, appropriate carbohydrate and catalyst may be chosen and the reaction is conducted in a corresponding adapted temperature for the conversion of the carbohydrate to HMF or furfural. For example, if glucose is chosen as carbohydrate, chloride or bromide containing chromium (Cr) or tin (Sn) or chromium complex of N-heterocyclic carbine can be used as catalyst, converting glucose to HMF at about 100~120° C. If fructose or xylose is chosen as carbohydrate, acid catalyst, chloride or bromide containing chromium (Cr) or tin (Sn), or chromium complex of N-heterocyclic carbene can be used as catalyst, converting fructose or xylose to HMF or furfural at about 80~100° C. While when starch or cellulose is used as carbohydrate, the used catalyst is chloride or bromide containing chromium (Cr) or tin (Sn), and the starch or cellulose is converted to HMF at about 120~140° C.

The relative experimental examples of preparation of HMF or furfural and the mixture for preparing the same are disclosed as follows. However, It will be apparent to those skilled in the art that the contents of examples, such as the steps and the materials, should be considered as exemplary only. The disclosure is not intended to limit the protection. Various modifications and variations can be made to the disclosed embodiments.

Example 1

Choline chloride and various hydroxyl organic solvents were mixed, and glucose was converted to HMF using a Chromium(II) chloride ($CrCl_2$) catalyst.

Choline chloride was used as organic ammonium salt, $CrCl_2$ was used as catalyst, and glucose was used as carbohydrate in Example 1. Choline chloride and various hydroxyl organic solvents were mixed according to the molar ratio needed and heated to 100° C. (the heating temperature was lower than 120° C.) to form a solution. The solution was mixed with glucose, and $CrCl_2$ catalyst (with amount based on the mole of the glucose) was added. The reaction was conducted at 100° C. (the conversion temperature was, for example, 100~120° C.), and glucose was converted to the product HMF. The experimental conditions and the experimental results of HMF yields in the Example 1 are listed in Table 2.

1,3-propylene glycol was used as hydroxyl organic solvent in Example 1-1, 1,4-butanediol was used as hydroxyl organic solvent in Example 1-2, diethylene glycol was used as hydroxyl organic solvent in Example 1-3, PEG200 (polyethylene glycol 200) was used as hydroxyl organic solvent in Example 1-4, and glycerol was used as hydroxyl organic solvent in Example 1-5. Table 2 shows that the yields of HMF were over 30%, even over 50%.

TABLE 1

| Carbohydrates | Selectively added catalysts |
| --- | --- |
| hexose, disaccharose, oligosaccharide, glycan, fructose, glucose, sucrose, starch | 1. chloride or bromide containing chromium (Cr) or tin (Sn), or<br>2. chromium complex of N-heterocyclic carbene |
| fructose, pentose or xylose | 1. acid catalyst,<br>2. chloride or bromide containing chromium (Cr) or tin (Sn), or<br>3. chromium complex of N-heterocyclic carbene |

TABLE 2

| | Example | | | | |
| --- | --- | --- | --- | --- | --- |
| | 1-1 | 1-2 | 1-3 | 1-4 | 1-5 |
| Organic ammonium salt (A) | choline chloride | choline chloride | choline chloride | choline chloride | choline chloride |
| Hydroxyl organic solvent (B) | 1,3-propylene glycol | 1,4-butanediol | diethylene glycol | PEG200 | glycerol |
| [A]/[A + B] (mol %) | 50 | 50 | 50 | 50 | 67 |
| [catalyst] (based on the mol % of glucose) | 6 | 10 | 6 | 10 | 6 |

TABLE 2-continued

| | Example | | | | |
|---|---|---|---|---|---|
| | 1-1 | 1-2 | 1-3 | 1-4 | 1-5 |
| [glucose] (wt %) | 5.7 | 5.7 | 5.7 | 5.7 | 5.7 |
| Reaction time (min) | 120 | 120 | 180 | 60 | 180 |
| Conversion fraction of glucose (%) | 73 | 99 | 89 | 92 | 94 |
| Yield of HMF (mol %) | 40 | 54 | 56 | 54 | 32 |

Example 2

Choline chloride and diethylene glycol solvent were mixed at various ratio or the concentration of glucose was changed. Glucose was converted to HMF using a $CrCl_2$ catalyst.

Choline chloride was used as organic ammonium salt, diethylene glycol was used as hydroxyl organic solvent, $CrCl_2$ was used as catalyst, and glucose was used as carbohydrate in Example 2. Choline chloride and diethylene glycol solvent were mixed according to the molar ratio needed and heated to 100° C. to form a solution. The solution was mixed with glucose, and 6 mol % $CrCl_2$ catalyst (with amount based on the mole of the glucose) was added. The reaction was conducted at 100° C., and glucose was converted to the product HMF.

The experimental conditions and the experimental results of HMF yields in the Example 2 are listed in Table 3. The yield of HMF in Example 2-1~2-3 was 57%, 61% and 56%, respectively.

TABLE 3

| | Example | | |
|---|---|---|---|
| | 2-1 | 2-2 | 2-3 |
| Organic ammonium salt (A) | choline chloride | choline chloride | choline chloride |
| Hydroxyl organic solvent (B) | diethylene glycol | diethylene glycol | diethylene glycol |

TABLE 3-continued

| | Example | | |
|---|---|---|---|
| | 2-1 | 2-2 | 2-3 |
| [A]/[A + B] (mol %) | 60 | 67 | 75 |
| [catalyst] (based on the mol % of glucose) | 6 | 6 | 6 |
| [glucose] (wt %) | 5.7 | 5.7 | 10 |
| Reaction time (min) | 180 | 300 | 120 |
| Conversion fraction of glucose (%) | 91 | 94 | 96 |
| Yield of HMF (mol %) | 57 | 61 | 56 |

Example 3

Various organic ammonium salts and various hydroxyl organic solvents were mixed at various ratio. Glucose was converted to HMF using a $CrCl_2$ catalyst.

Various organic ammonium salts were used, diethylene glycol (Example 3-1~3-3, 3-5 and 3-6), or PEG200 (Example 3-4) was used as hydroxyl organic solvent, $CrCl_2$ was used as catalyst, and glucose was used as carbohydrate in Example 3. Various organic ammonium salts and various hydroxyl organic solvents were mixed according to the molar ratio needed and heated to 100° C. to form a solution. The solution was mixed with glucose, and $CrCl_2$ catalyst (with amount based on the mole of the glucose) was added. The reaction was conducted at 100° C., and glucose was converted to the product HMF. The experimental conditions and the experimental results of HMF yields in the Example 3 are listed in Table 4.

Triethylmethylammonium chloride (TEMAC) was used as organic ammonium salt in Example 3-1, benzyltriethylammonium chloride (BTEAC) was used as organic ammonium salt in Example 3-2~3-4, benzyltributylammonium bromide (BTBAB) was used as organic ammonium salt in Example 3-5, and 1-butylpyridinium chloride (BPyC) was used as organic ammonium salt in Example 3-6. All of them can convert glucose to HMF efficiently. The yields of HMF can reach 75% and 74% in Example 3-1 and 3-4, respectively.

TABLE 4

| | Example | | | | | |
|---|---|---|---|---|---|---|
| | 3-1 | 3-2 | 3-3 | 3-4 | 3-5 | 3-6 |
| Organic ammonium salt (A) | TEMAC | BTEAC | BTEAC | BTEAC | BTBAB | BPyC |
| Hydroxyl organic solvent (B) | diethylene glycol | diethylene glycol | diethylene glycol | PEG200 | diethylene glycol | diethylene glycol |
| [A]/[A + B] (mol %) | 67 | 67 | 75 | 82 | 67 | 75 |
| [catalyst] (based on the mol % of glucose) | 6 | 6 | 10 | 6 | 6 | 6 |
| [glucose] (wt %) | 10 | 5.7 | 5.7 | 5.7 | 10 | 10 |
| Reaction time (min) | 120 | 180 | 120 | 240 | 180 | 120 |

TABLE 4-continued

| | Example | | | | | |
|---|---|---|---|---|---|---|
| | 3-1 | 3-2 | 3-3 | 3-4 | 3-5 | 3-6 |
| Conversion fraction of glucose (%) | 97 | 98 | 97 | 96 | 95 | 99 |
| Yield of HMF (mol %) | 75 | 68 | 65 | 74 | 45 | 64 |

Example 4

Organic ammonium salt and hydroxyl organic solvent were mixed, and glucose was converted to HMF using various catalyst.

Choline chloride (Example 4-1~4-2) or benzyltriethylammonium chloride (BTEAC, used in Example 4-3~4-5) was used as organic ammonium salt, diethylene glycol (Example 4-1~4-3) or PEG200 (Example 4-4~4-5) was used as hydroxyl organic solvent, and glucose was used as carbohydrate in Example 4. Glucose was converted to HMF using various catalyst, for example, chromium(III) chloride hydrate ($CrCl_3 \cdot 6H_2O$), tin(IV) chloride pentahydrate ($SnCl_4 \cdot 5H_2O$), chromium(III) bromide hexahydrate ($CrBr_3 \cdot 6H_2O$), and a complex of 1,3-bis(2,6-bisisopropylphenyl)imidazolium chloride/$CrCl_2$ (abbreviated as Cr-carbene). Organic ammonium salt and hydroxyl organic solvent were mixed according to the molar ratio needed and heated to 100° C. to form a solution. The solution was mixed with glucose, and the catalyst (with amount based on the mole of the glucose, while wt % was used as unit of catalyst concentration in Example 4-5) was added. The reaction was conducted at 100° C., and glucose was converted to the product HMF. The experimental conditions and the experimental results of HMF yields in the Example 4 are listed in Table 5. The yields of HMF can reach 65% and 66% in Example 4-3 and 4-4, respectively.

Example 5

Organic ammonium salt and hydroxyl organic solvent were mixed, and fructose was converted to HMF using acid catalyst.

Choline chloride (Example 5-1 and 5-3) or benzyltriethylammonium chloride (BTEAC, used in Example 5-2) was used as organic ammonium salt, diethylene glycol (Example 5-1 and 5-2) or ethylene glycol (Example 5-3) was used as hydroxyl organic solvent, Amberlyst-15 (AMBERLYST™ Polymeric Catalysts, abbreviated as Am-15, and available from Rohm and Haas Co., U.S.) was used as sulfonic acid ion-exchange resin catalyst, and fructose was used as carbohydrate in Example 5. As demonstrated in Example 5-1, choline chloride, the organic ammonium salt used, was mixed with diethylene glycol solvent at the ratio 75 mol % and heated to 100° C. to form a solution. The solution was mixed with fructose, and catalyst (with amount based on the weight ratio of the fructose) was added. The reaction was conducted at 80° C., and fructose was converted to the product HMF. Similar steps were performed in Example 5-2 and 5-3. The experimental conditions and the experimental results of HMF yields in the Example 5 are listed in Table 6.

The yield of HMF can reach 72%, 80% and 73% in Example 5-1, 5-2 and 5-3, respectively.

TABLE 5

| | Example | | | | | |
|---|---|---|---|---|---|---|
| | 4-1 | 4-2 | 4-3 | 4-4 | Example | 4-5 |
| Organic ammonium salt (A) | choline chloride | choline chloride | BTEAC | BTEAC | Organic ammonium salt (A) | BTEAC |
| Hydroxyl organic solvent (B) | diethylene glycol | diethylene glycol | diethylene glycol | PEG200 | Hydroxyl organic solvent (B) | PEG200 |
| [A]/[A + B] (mol %) | 50 | 50 | 75 | 83 | [A]/[A + B] (mol %) | 83 |
| Catalyst | $CrCl_3 \cdot 6H_2O$ | $SnCl_4 \cdot 5H_2O$ | $CrBr_3 \cdot 6H_2O$ | $CrCl_3 \cdot 6H_2O$ | | Cr-carbene |
| [catalyst] (based on the mol % of glucose) | 10 | 10 | 6 | 6 | [catalyst] | 50 wt % |
| [glucose] (wt %) | 10 | 10 | 10 | 10 | [glucose] (wt %) | 10 |
| Reaction time (min) | 180 | 180 | 60 | 60 | Reaction time (min) | 360 |
| Conversion fraction of glucose (%) | 91 | 81 | 97 | 97 | Conversion fraction of glucose (%) | 67 |
| Yield of HMF (mol %) | 43 | 36 | 65 | 66 | Yield of HMF (mol %) | 35 |

TABLE 6

| | Example | | |
|---|---|---|---|
| | 5-1 | 5-2 | 5-3 |
| Organic ammonium salt (A) | choline chloride | BTEAC | BTEAC |
| Hydroxyl organic solvent (B) | diethylene glycol | diethylene glycol | ethylene glycol |
| [A]/[A + B] (mol %) | 75 | 71 | 75 |
| Catalyst | Am-15 | Am-15 | Am-15 |
| [catalyst] (based on fructose, wt/wt) | 1:2 | 1:5 | 1:5 |
| [fructose] (wt %) | 10 | 10 | 10 |
| Reaction time (min) | 60 | 60 | 60 |
| Conversion fraction of fructose (%) | 100 | 99 | 100 |
| Yield of HMF (mol %) | 72 | 80 | 73 |

Example 6

Organic ammonium salt and diethylene glycol solvent were mixed, and various carbohydrates were converted to HMF using catalyst.

Choline chloride (Example 6-1 and 6-2) or benzyltriethylammonium chloride (BTEAC, used in Example 6-3) was used as organic ammonium salt, diethylene glycol was used as hydroxyl organic solvent, $CrCl_2$ (Example 6-1 and 6-3) or $CrCl_3 \cdot 6H_2O$ (Example 6-2) was used as catalyst, and sucrose, starch or xylose was used as carbohydrate in Example 6. Organic ammonium salt was mixed with diethylene glycol solvent at the ratio 75 mol % and heated to 100° C. to form a solution. The solution was mixed with sucrose, starch or xylose, and 6 mol % catalyst (with amount based on the mole of the carbohydrate) was added. The reactions were conducted at the temperature of 100° C., for sucrose, 120° C. for starch, and 100° C. for xylose, respectively. And sucrose, starch, or xylose was converted to the product HMF. The experimental conditions and the experimental results of HMF yields in the Example 6 are listed in Table 7. The yield of HMF can reach 69% in Example 6-1.

TABLE 7

| | Example | | |
|---|---|---|---|
| | 6-1 | 6-2 | 6-3 |
| Organic ammonium salt (A) | choline chloride | choline chloride | BTEAC |
| Hydroxyl organic solvent (B) | diethylene glycol | diethylene glycol | ethylene glycol |
| [A]/[A + B] (mol %) | 75 | 75 | 75 |
| Catalyst | $CrCl_2$ | $CrCl_3 \cdot 6H_2O$ | $CrCl_2$ |
| [catalyst] (based on fructose, mol %) | 6 | 6 | 1:5 |
| [carbohydrate] (wt %) | Sucrose 10% | Starch 10% | Xylose 10% |
| Reaction time (min) | 60 | 120 | 30 |
| Conversion fraction of carbohydrate (%) | — | — | 96 |
| Yield of HMF (mol %) | 69 | 39 | 51 |

Compared to the traditional preparation, the preparation disclosed in the embodiment is different to the well-known ionic liquid system, which the melting point of used organic ammonium salt must lower than 100° C. The preparation of HMF or furfural disclosed in the embodiment is mixing organic ammonium salt and hydroxyl organic solvent according to the suitable molar ratio to form a solution, of which the melting temperature is lower than 100° C. Then the solution is mixed with carbohydrate (for example, fructose or glucose) to form a mixture. The mixture is then heated for the conversion of carbohydrate to the product HMF or furfural. According to the synthesis method provided in the embodiments, at least 20 mol %, or much higher yield of HMF or furfural can be achieved. Since the non-commercial produced, expensive ionic liquid is not used in the disclosed preparation for HMF according to the embodiments, the production cost is thus decreased compared to the traditional preparation using expensive ionic liquid.

While the disclosure has been described by way of example and in terms of the exemplary embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method of preparing furfural compounds, comprising:
   forming a solution by mixing an organic ammonium salt and a hydroxyl organic solvent, wherein the organic ammonium salt is at least one of the compounds represented by the general chemical formulas [I], [II], [III] or [IV]:

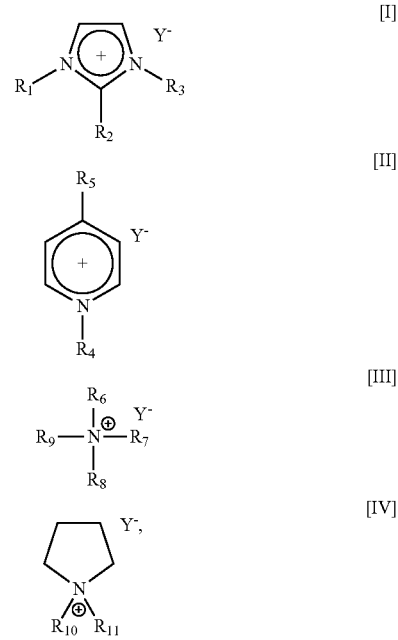

wherein $R_1$~$R_{11}$ are independently selected from hydrogen (H), alkyl functional groups, cycloalkyl functional groups, aryl functional groups, and alkaryl functional groups, and the functional groups optionally connect to hydrogen, OH, Cl, Br, I, or CN, and the organic ammonium salt has a melting temperature >100° C., and
   wherein the hydroxyl solvent comprises $C_2$-$C_6$ compounds of diols, triols, or polyalcohols;
   forming a mixture by added a carbohydrate to the solution, wherein the mixture further comprises a catalyst, the catalyst is chloride or bromide containing chromium compounds, chloride or bromide containing tin compounds, chromium complex of N-heterocyclic carbine, zeolite, or sulfonic acid ion-exchange resin catalyst; and heating the mixture to a reaction temperature for conversion of the carbohydrate to the furfural compounds.

2. The method according to claim 1, wherein the anion Y⁻ of the organic ammonium salt is F⁻, Cl⁻, Br⁻, I⁻, $NO_3^-$, $HSO_4^-$, $BF_4^-$, CN⁻, $SO_3CF_3^-$, or $COOCF_3^-$.

3. The method according to claim 1, wherein the organic ammonium salt comprises cycloalkyltrialkylammonium salt, aryltrialkylammonium salt, alkaryltrialkylammonium salt, tetraalkylammonium salt, or the combinations thereof.

4. The method according to claim 1, wherein the organic ammonium salt is a heterocyclic ring-contained organic ammonium salt, and the heterocyclic ring-contained organic ammonium salt comprises a pyridinium functional group, an imidazolium functional group, or a pyrrolidinium functional group.

5. The method according to claim 1, wherein the reaction temperature is below 180° C.

6. A mixture for preparing furfural compounds, comprising an organic ammonium salt, a hydroxyl organic solvent, a carbohydrate and a catalyst, wherein the organic ammonium salt is at least one of the compounds represented by the general chemical formulas [I], [II], [III] or [IV]:

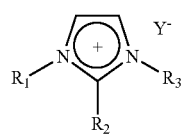

[I]

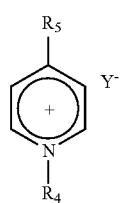

[II]

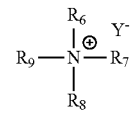

[III]

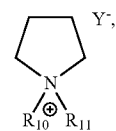

[IV]

wherein $R_1$~$R_{11}$ are independently selected from hydrogen (H), alkyl functional groups, cycloalkyl functional groups, aryl functional groups, and alkaryl functional groups, and the functional groups optionally connect to hydrogen, OH, Cl, Br, I, or CN, and the organic ammonium salt has a melting temperature >100° C., wherein the hydroxyl organic solvent comprises $C_2$-$C_6$ compounds of diols, triols, or polyalcohols, wherein the catalyst is chloride or bromide containing chromium compounds, chloride or bromide containing tin compounds, chromium complex of N-heterocyclic carbine, zeolite, or sulfonic acid ion-exchange resin catalyst, wherein a molar ratio of the organic ammonium salt to the hydroxyl organic solvent is in a range of 1 to 9, and wherein the amount of the carbohydrate is 5~20 wt % of the mixture.

7. The mixture according to claim 6, wherein Y⁻ of the organic ammonium salt is F⁻, Cl⁻, Br⁻, I⁻, $NO_3^-$, $HSO_4^-$, $BF_4^-$, CN⁻, $SO_3CF_3^-$, or $COOCF_3^-$.

8. The mixture according to claim 6, wherein the organic ammonium salt comprises cycloalkyltrialkylammonium salt, aryltrialkylammonium salt, alkaryltrialkylammonium salt, tetraalkylammonium salt, or the combinations thereof.

9. The mixture according to claim 6, wherein the organic ammonium salt is a heterocyclic ring-contained organic ammonium salt, and the heterocyclic ring-contained organic ammonium salt comprises a pyridinium functional group, an imidazolium functional group, or a pyrrolidinium functional group.

* * * * *